(12) United States Patent
Feldman

(10) Patent No.: US 12,653,723 B2
(45) Date of Patent: Jun. 16, 2026

(54) DEVICE FOR USE WITH INGROWN TOENAIL RELIEF

(71) Applicant: PROFOOT, INC., Elizabeth, NJ (US)

(72) Inventor: Daniel Feldman, Elizabeth, NJ (US)

( * ) Notice: Subject to any disclaimer, the term of this patent is extended or adjusted under 35 U.S.C. 154(b) by 0 days.

(21) Appl. No.: 17/365,545

(22) Filed: Jul. 1, 2021

(65) Prior Publication Data

US 2023/0000691 A1    Jan. 5, 2023

(51) Int. Cl.
      *A61F 13/06*      (2006.01)
      *A61F 13/00*      (2024.01)
      *A61F 13/0246*    (2024.01)

(52) U.S. Cl.
      CPC ...... *A61F 13/068* (2013.01); *A61F 13/00063* (2013.01); *A61F 13/0253* (2013.01)

(58) Field of Classification Search
      CPC .............. A61F 13/068; A61F 13/00063; A61F 13/0253; A61F 2013/00353; A61F 2013/00285; A61F 2013/0017; A61F 13/105; A61F 13/063; A61F 13/10; A61M 35/00
      See application file for complete search history.

(56) References Cited

U.S. PATENT DOCUMENTS

| | | | |
|---|---|---|---|
| 2,781,044 A | 2/1957 | Bennett | |
| 3,464,408 A | 9/1969 | Hamlin | |
| 3,765,410 A * | 10/1973 | Berens | A61F 5/11 |
| | | | 602/31 |
| 3,799,160 A | 3/1974 | Hahn | |

(Continued)

FOREIGN PATENT DOCUMENTS

| | | |
|---|---|---|
| AT | 16302 U1 | 6/2019 |
| WO | 1994016991 A1 | 8/1994 |

(Continued)

OTHER PUBLICATIONS

Kuncir et al., Load-bearing Characteristics of Polyethylene Foam, 1990, Journal of Rehabilitation Research and Development, vol. 27 No. 3, pp. 229-238 (Year: 1990).*

(Continued)

*Primary Examiner* — Catharine L Anderson
*Assistant Examiner* — Peter Daniel Smith
(74) *Attorney, Agent, or Firm* — Fitch, Even, Tabin & Flannery, LLP

(57) ABSTRACT

A bandage is provided having a flexible and wrapable bandage strip coated on one side with pressure sensitive adhesive, and on the same side as the pressure sensitive adhesive a compressible and expandable composition retaining well having an aperture configured to receive a medicated gel composition is affixed at its base about midway along a length of the strip; wherein the composition retaining well at rest is about 3 millimeters to 10 millimeters in height from its base to the aperture and having sides sloping towards the aperture of about 30 degrees to about 80 degrees. In one embodiment the strip and the composition retaining well can be integral. The composition retaining well can be compressible from about 20 to 80 percent of its height at rest. The composition retaining well can be made from an inert material and made of any suitable moisture-blocking material.

9 Claims, 2 Drawing Sheets

(56) References Cited

U.S. PATENT DOCUMENTS

| | | | | |
|---|---|---|---|---|
| 4,005,709 | A * | 2/1977 | Laerdal | A61F 13/01021 |
| | | | | 602/53 |
| 4,377,159 | A * | 3/1983 | Hansen | A61F 13/0203 |
| | | | | 602/53 |
| 5,394,890 | A | 3/1995 | Lambert | |
| 5,948,392 | A * | 9/1999 | Haslwanter | A61K 8/23 |
| | | | | 424/707 |
| 10,092,297 | B2 * | 10/2018 | Hoff | A61B 17/1325 |
| 2006/0105028 | A1 * | 5/2006 | Zhang | A61K 9/7084 |
| | | | | 424/448 |
| 2007/0287945 | A1 | 12/2007 | Cha | |
| 2009/0048551 | A1 | 2/2009 | Liberson | |
| 2009/0088707 | A1 * | 4/2009 | Adams | A61F 13/10 |
| | | | | 604/307 |
| 2010/0222728 | A1 * | 9/2010 | Brooks | A61F 13/068 |
| | | | | 602/30 |
| 2013/0030343 | A1 * | 1/2013 | Antalek | A61F 13/0226 |
| | | | | 602/60 |
| 2013/0138055 | A1 | 5/2013 | Samlaska | |
| 2016/0220507 | A1 * | 8/2016 | Zhang | A61K 9/06 |
| 2017/0216079 | A1 | 8/2017 | Harada | |
| 2022/0125645 | A1 * | 4/2022 | Di Palo | A61F 13/8405 |
| 2022/0133544 | A1 * | 5/2022 | Turton | A61F 13/00063 |
| | | | | 604/372 |

FOREIGN PATENT DOCUMENTS

| | | |
|---|---|---|
| WO | 2000057845 A1 | 10/2000 |
| WO | 2013066275 A1 | 5/2013 |

OTHER PUBLICATIONS

Kuncir et al., Load-bearing characteristics of polyethylene foam, Journal of Rehabilitation Research and Development vol. 27 No. 3, 1990 pp. 229-238 (Year: 1990).*

* cited by examiner

DEVICE FOR USE WITH INGROWN TOENAIL RELIEF

FIELD

Presented herein are devices and methods for use in relieving pain associated with ingrown toenails, and in particular devices and methods for relieving ingrown toenails using a bandage wrap having a compressible/expandable well configured to receive over-the-counter (OTC) ingrown toenail relief products.

BACKGROUND

Onychocryptosis is a nail condition where a lateral edge of a nail plate pierces tissue in or directly under a lateral nail fold. This condition is more commonly known as an ingrown toenail. Ingrown toenails can develop when the distal portion of the toenail is cut too short, thereby allowing the cuticle and toe flesh at the corner of the emerging toenail (rear corner terminus of the free portion of the toenail) to overlap the toenail, thus causing inflammation, swelling and pain.

Sulfides, such as sodium sulfide nonahydrate, (hereinafter referred to as sodium sulfide), are effective keratolytic agents for softening nails. According to the Federal Register, over-the-counter ingrown toenail relief drug products in a form suitable for topical administration can, under certain circumstances, be generally recognized as safe and effective (for example sodium sulfide 1 percent in a gel vehicle). (See generally, Federal Register Vol. 68, No. 88, May 7, 2003; pages 24347-24349)

Various medicated devices and methods using, for example, sodium sulfide or conventional antibiotics such as mercurochrome have been provided to correct or relieve pain associated with an ingrown toenail (See, generally, U.S. Pat. Nos. 5,770,583; 3,464,408 and 3,799,160). However, most such devices either are complicated to use, expensive or of little practical value. For example, the device may not be able to adequately and deliberately direct and hold the medication on the affected area and may not provide a sufficient quantity of medication.

Accordingly, it would be desirable to provide a simple, inexpensive, but highly effective device for such purposes and a simple method of use of the same. Preferably, such a device should be easily applied to an affected area and easily disposable.

It is to be understood that if any prior art information is referred to herein, such reference does not constitute an admission that the information forms part of the common general knowledge in the art.

SUMMARY

Accordingly, to advance at least the aforementioned deficiencies in the art, described herein is a simple, easily used, wrapable bandage for use in relieving pain associated with ingrown toenails. The present embodiments provide a device to deliberately and effectively direct and hold a sufficient quantity of medication against an affected area, such as an ingrown toenail.

According to one approach, a bandage is provided having a flexible and wrapable bandage strip coated on one side with pressure sensitive adhesive, and on the same side as the pressure sensitive adhesive a compressible and expandable composition retaining well having an aperture configured to receive a medicated gel composition is affixed at its base about midway along a length of the strip; wherein the composition retaining well at rest is about 3 millimeters to 10 millimeters in height from its base to the aperture and having sides sloping towards the aperture of about 30 degrees to about 80 degrees. In one embodiment the strip and the composition retaining well can be integral.

In various embodiments, the composition retaining well can be compressible from about 20 to 80 percent of its height at rest. The well depth can be between 100 percent to 50 percent of the height of the composition retaining well. The composition retaining well can be made from an inert material and made of any suitable moisture-blocking material. The composition retaining well can be selected from the group consisting of polyethylene foam, closed foam, vinyl film, low density polyethylene foam, and the like, and combinations thereof. The strip can be selected from the group consisting of rubber, a breathable polymeric material, a woven tricot cloth, vinyl film, cellulose and plastic web. The composition retaining well can be configured to receive a medicated gel having 1 percent sodium sulfide.

According to one approach, a method of relieving pain associated with ingrown toenails may have the steps of providing a bandage having a flexible and wrapable bandage strip coated on one side with pressure sensitive adhesive, and on the same side as the pressure sensitive adhesive a compressible and expandable composition retaining well having an aperture configured to receive a medicated gel composition is affixed at its base about midway along a length of the strip; wherein the composition retaining well at rest is about 3 millimeters to 10 millimeters in height from its base to the aperture and having sides sloping towards the aperture of about 30 degrees to about 80 degrees; providing a tube of a medicated gel having 1 percent sodium sulfide; squeezing gel into the well until it is about 50 to 100 percent filled; aligning the aperture over an affected area of the toenail; compressing the composition retaining well adjacent to the affected area; and wrapping the strip around the toe and releasably affixing the strip to the toe by the pressure sensitive adhesive.

According to another approach, an ingrown toenail relief kit is provided having a bandage having a flexible and wrapable bandage strip coated on one side with pressure sensitive adhesive, and on the same side as the pressure sensitive adhesive a compressible and expandable composition retaining well having an aperture configured to receive a medicated gel composition is affixed at its base about midway along a length of the strip; wherein the composition retaining well at rest is about 3 millimeters to 10 millimeters in height from its base to the aperture and having sides sloping towards the aperture of about 30 degrees to about 80 degrees; and a tube of a medicated gel having 1 percent sodium sulfide.

Other aspects of the invention are also disclosed and will become more apparent to persons having ordinary skill in the art to which the devices pertain and from the following description and claims.

BRIEF DESCRIPTION OF THE DRAWINGS

Notwithstanding any other forms which may fall within the scope of the present invention, preferred embodiments of the disclosure will now be described, by way of example only, with reference to the accompanying drawings in which.

Figures 1, 2:
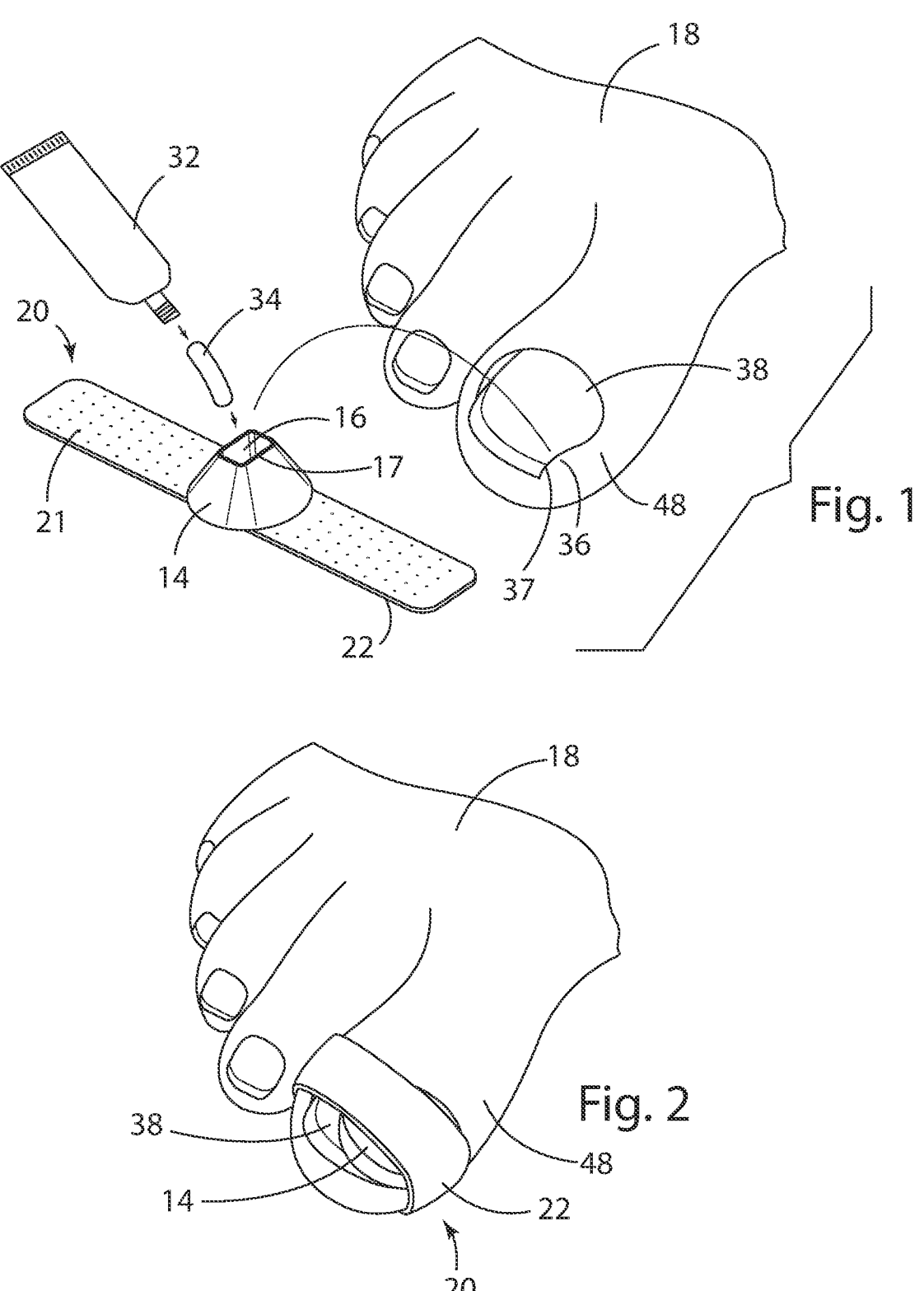
FIG. 1 illustrates a perspective view of a device in accordance with one of the present embodiments in use.
FIG. 2 illustrates a perspective view of a device in accordance with the present embodiment of FIG. 1 applied to a user.

While the features described herein may be susceptible to various modifications and alternative forms, specific embodiments thereof are shown by way of example in the drawings and are herein described in detail. It should be understood, however, that the drawings and detailed description thereto are not intended to be limiting to the particular form disclosed, but on the contrary, the intention is to cover all modifications, equivalents and alternatives falling within the spirit and scope of the subject matter as defined by at least the appended claims.

DETAILED DESCRIPTION

The present embodiments provide a flexible strip having on one side a pressure sensitive adhesive and a compressible/expandable well to receive compositions therein. In use, the pressure sensitive adhesive may be applied to a surface to hold and compress the well against the surface thereby exposing the surface adjacent the opening/aperture of the well to the composition contained therein. Although the present embodiments are demonstrated as a bandage wrap having a compressible/expandable well configured to receive over-the-counter (OTC) ingrown toenail relief products, it is understood that present embodiments may be used wherever any composition is desired to be maintained adjacent a surface.

Thus, accordingly to one exemplary approach, presented herein are simple easy to use devices configured to assist in relieving pain associated with ingrown toenails by deliberately and effectively applying medication disposed within a compressible/expandable well against an affected area.

The present figures provide an exemplary use of the device of the present embodiments. A device 20 (shown herein as a bandage wrap) is comprised of a flexible/wrapable bandage strip 22 coated on one side with pressure sensitive adhesive 21. Pressure sensitive adhesive 21, can be a permanently tacky material like an acrylic adhesive, rubber base adhesive, or the like. Pressure sensitive adhesive 21 functions as an attaching means for releasably holding device 20 in place around a toe 48 so that an aperture of a well having a medicated gel can be directly, firmly and consistently applied to an affected area.

Strip 22 can be made of rubber, a breathable polymeric material, a woven tricot cloth, vinyl film, cellulose, plastic web and the like so long as it is flexible and wrapable, and optionally stretchable. Strip 22 has on the same side as the pressure sensitive adhesive a composition retaining well 14 having a well/opening/bore 16, the underside/base of which is attached to strip 22 either by the pressure sensitive adhesive 21 or by a separate more permanent adhesive (not shown). Composition retaining well 14 should be an essentially inert material and can be made of any suitable moisture-blocking material, such as polyethylene foam, closed foam, vinyl film, low density polyethylene foam, and the like.

In FIG. 1, foot 18 is depicted as having a nail 38 on toe 48 having an ingrown portion 36, which pierces the nail groove 37. A sulfide-containing gel 34 from tube 32 is squeezed into composition well 16. For exemplary purposes, gel 34 may be a sulfide, a polysulfide or mixtures thereof, of an alkali or an alkaline earth metal and a carrier which is an aqueous or water-containing formulation of a modified cellulosic material within which the sulfide is dissolved or dispersed and in which the utilized water is deionized and/or distilled.

In FIG. 2, device 20 with gel 34 disposed in composition well 16 is wrapped around the user's toe 38 and held in place by the pressure sensitive adhesive aligned with the afflicted nail groove 37 of ingrown toenail 36. As shown in FIG. 2, composition retaining well 14 has been compressed about 20-80 percent of its height 24 at rest (See FIG. 4). Device 20 thus retains gel 34 in the area of nail groove 37 on nail 38 with a firm consistent force. As the composition retaining well 14 is compressed the top is compressed to form a seal around the affected area. At this stage the sealing compression does not require much effort by the user since the composition retaining well 14 is relatively narrow at its top. As more pressure is applied, the base of composition retaining well 14 expands to apply greater pressure to drive the medicated gel deeper into the affected area.

As shown in the figures, composition retaining well 14 may be a pyramid or a cone shape or any variation between a pyramid and cone shape. The cone base may be round or oblong and the pyramid base may be square or rectangular. The angles of slopes 28 (FIG. 4) and 30 (FIG. 8) of composition retaining well 14 may be 30 degrees to about 80 degrees. The base dimension 26 (FIG. 4) of composition retaining well 14 can vary from about 8 millimeters to 20 millimeters. Composition retaining well 14 can vary from 3 millimeters to 10 millimeters in thickness while at rest and compressible as mentioned above combined thickness of strip 22 can be a thickness 24 that can vary from 3 millimeters to 12 millimeters.

Composition retaining well 14 not only protects the skin and retains the sulfide-containing gel in place on the afflicted ingrown toenail area, but also through the compression of composition retaining well 14 adds a greater, more effective seal and greater and more effective pressure of gel 34 onto the affected area of nail 38. Thus, the present embodiments provide a superior ability to seal and drive medicated gels into affected areas. The exposed portion of composition retaining well 14 may optionally also have has a pressure sensitive adhesive for attaching to the toe.

Well 16 depth 44 (FIG. 5) may vary by as much as 100 percent to 50 percent of height 24 of composition retaining well 14. Well 16 can be a generally rectangular/oblong slot or aperture defining the opening of well 16. Dimensions of the aperture 17 of well 16 are configured to cover an affected area with the composition. Accordingly, aperture 17 should be sized to cover most ingrown toenails (e.g., 2-3 millimeters in width 42 and 5-12 millimeters in length 40, See FIG. 3). It is noted that the largest dimension of well 16 should be perpendicular to the axis 46 (FIG. 7) of strip 22.

Figures 3, 4, 5, 6, 7, 8:
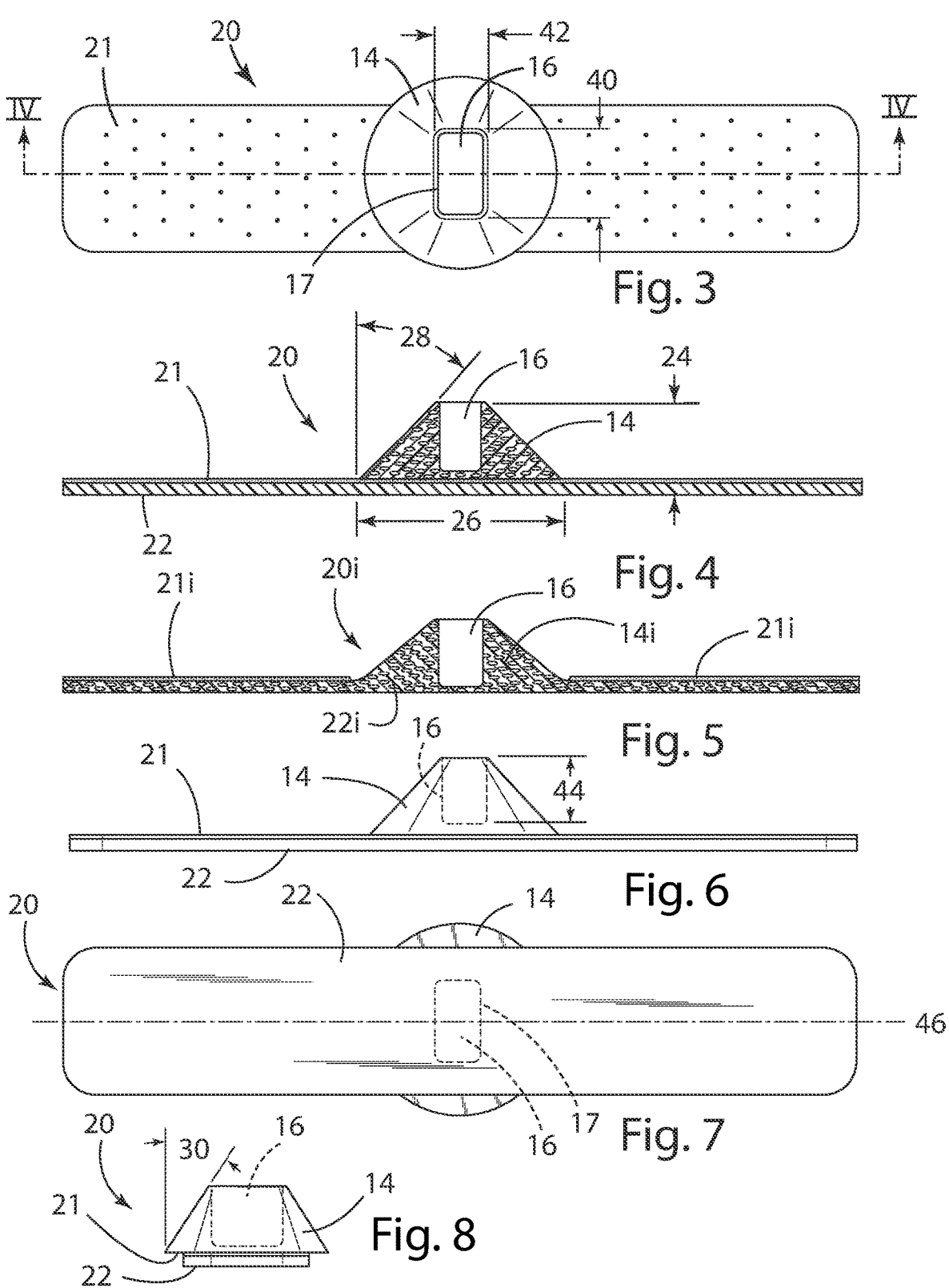
FIG. 3 illustrates a top view of a device in accordance with the present embodiment of FIG. 1.
FIG. 4 illustrates a sectional view of the device in accordance with the present embodiment of FIG. 1 taken along section lines IV-IV of FIG. 3.
FIG. 5 illustrates a sectional view of the device in accordance with an alternate embodiment taken along section lines IV-IV of FIG. 3.
FIG. 6 illustrates a front elevation view of a device in accordance with the present embodiment of FIG. 1.
FIG. 7 illustrates a bottom view of a device in accordance with the present embodiment of FIG. 1.
FIG. 8 illustrates a side elevation view of a device in accordance with the present embodiment of FIG. 1.

FIG. 5 shows an alternate embodiment of device 20. In this embodiment, strip 22 and composition retaining well 14 are integral.

The foregoing description, for purposes of explanation, used specific nomenclature to provide a thorough understanding of the invention. However, it will be apparent to one skilled in the art that specific details are not required in order to practice the invention. Thus, the foregoing descriptions of specific embodiments of the invention are presented for purposes of illustration and description. They are not intended to be exhaustive or to limit the invention to the precise forms disclosed as obviously many modifications and variations are possible in view of the above teachings. The embodiments were chosen and described in order to best explain the principles of the invention and its practical applications, thereby enabling others skilled in the art to best utilize the invention and various embodiments with various modifications as are suited to the particular use contemplated. It is intended that the following claims and their equivalents define the scope of the invention. The term "approximately" or similar as used herein should be construed as being within 10% of the value stated unless otherwise indicated.

The drawings and the foregoing descriptions are not intended to represent the only forms of assemblies in regard to the details of construction. Changes in form and in proportion of parts, as well as the substitution of equivalents, are contemplated as circumstances may suggest or render expedient. Throughout this specification and the drawings and figures associated with this specification, numerical labels of previously shown or discussed features may be reused in another drawing figure to indicate similar features.

LIST OF REFERENCE NUMBERS 14 composition retaining well
16 composition well
17 well aperture
18 user foot
20 device/bandage wrap
21 pressure sensitive adhesive
22 bandage strip
24 composition retainer height
26 composition retainer width
28 composition retainer front angle
30 composition retainer side angle
32 composition tube
34 composition
36 ingrown portion of toenail
37 nail groove
38 toenail
40 well aperture length
42 well aperture width
44 well depth
46 strip 22 axis
48 toe

I claim:

1. A bandage, comprising:
a flexible and wrappable bandage strip comprising a first side with a first surface coated with pressure sensitive adhesive, and on the same side as the bandage strip pressure sensitive adhesive a compressible and expandable composition retaining well is affixed at a composition retaining well base about midway along a length of the bandage strip, the composition retaining well having an aperture at a distal end forming an opening of a composition retaining well cavity defined by a vertical cavity wall, the cavity configured to receive a medicated gel composition, wherein the composition retaining well base is made from an inert material and made of any suitable moisture-blocking material,
the composition retaining well base being shaped as one of a rectangle or oblong shape;
the composition retaining well base having an exterior wall tapering towards the aperture of the distal end at a taper angle of about 30 degrees to about 80 degrees from a composition retaining well base pyramid or cone shape;
wherein the exterior wall has a first taper along a first axis of the bandage and a second taper along a second axis,
wherein the first axis extends in the longitudinal direction of the bandage and the second axis extends perpendicular to the longitudinal direction and parallel to the first surface of the bandage;
wherein the first taper has a first taper angle and the second taper has a second taper angle, the first and second taper angles defined by the intersection of a first axis and a third axis perpendicular to the first axis and the second axis, wherein the first and second taper angles are about 30 degrees to 80 degrees from the third axis;
wherein the first taper angle and the second taper angle are different from each other within the 30 degrees to 80 degrees;
wherein the composition retaining well base at rest is about 3 millimeters to 10 millimeters in height from the base to the distal end;
wherein the composition retaining well base is compressible from about 20 to 80 percent of its height at rest when subjected to a compressive force;
wherein the composition retaining well base expands laterally in proportion to a proportionally increasing force to the composition retaining well base material as it compresses from 20 to 80 percent of its height, which expansion results in a proportional increasing reduction in the volume of the cavity from the proportionally increasing lateral contraction of the cavity wall;
wherein in use, the composition retaining well aperture is configured to first seal a periphery of a user's affected ingrown toenail area as pressure towards the user is first applied and as ever-increasing pressure is applied, the composition retaining well base proportionally expands laterally within the cavity to apply proportionally ever-increasing pressure within the cavity to drive the medicated gel composition ever deeper into the user's affected area.

2. The bandage of claim 1, wherein the strip and the composition retaining well base are integral.

3. The bandage of claim 1, wherein a cavity depth is between 100 percent to 50 percent of the height of composition retaining well base.

4. The bandage of claim 1, wherein the composition retaining well base is selected from a group consisting of polyethylene foam, closed foam, vinyl film, low density polyethylene foam, and combinations thereof.

5. The bandage of claim 1, wherein the strip is selected from a group consisting of rubber, a breathable polymeric material, a woven tricot cloth, vinyl film, cellulose and plastic web.

6. A method of relieving pain associated with ingrown toenails, the method comprising:
providing the bandage of claim 1;
providing a tube of a medicated gel having 1 percent sodium sulfide;

squeezing gel into the well until it is about 50 to 100 percent filled;

aligning the aperture over an affected area of the toenail;

compressing the composition retaining well base adjacent to the affected area to laterally expand; and wrapping the strip around the toe and releasably affixing the strip to the toe by the pressure sensitive adhesive.

7. An ingrown toenail relief kit comprising: the bandage of claim 1; and a tube of a medicated gel having 1 percent sodium sulfide.

8. The bandage of claim 1, wherein the medicated gel composition has 1 percent sodium sulfide, is disposed within the composition retaining well and is configured to provide relief to the user's ingrown toenail.

9. The bandage of claim 1, wherein the first axis is parallel to a longitudinal axis of the bandage, and wherein the degree of taper angle of the first axis is greater than the second axis.

* * * * *